US00PP10163P

United States Patent [19]

Gross

[11] Patent Number: Plant 10,163

[45] Date of Patent: Dec. 23, 1997

[54] POINSETTIA PLANT 'SOPHIE'

[75] Inventor: Eduard Gross, Nanteuillet, France

[73] Assignee: Paul Ecke Ranch, Inc., Encinitas, Calif.

[21] Appl. No.: 630,904

[22] Filed: Apr. 4, 1996

[51] Int. Cl.[6] ..... A01H 5/00

[52] U.S. Cl. ..... Plt./86.4

[58] Field of Search ..... Plt./86.4

[56] References Cited

PUBLICATIONS

UPOXROM citation, listing for 'Sophie' FR PBR 152116, Oct. 10, 1994.

*Primary Examiner*—James R. Feyrer

*Attorney, Agent, or Firm*—Arnold, White & Durkee

[57] ABSTRACT

Poinsettia 'Sophie' is a new cultivar, distinguished by bright red flower bracts, strong stems, even growth habit and self-branching chaacteristics. 'Sophie' is a sport of the red bracted 'Angelika' (U.S. Plant Pat. No. 5,492) with the same flowering response and cultural requirements. The new plant produces a very desirable branched flowering pot plant. The new plant is resistant to epinasty after being confined to shipping containers. The post-production foliage and bract retention are good.

1 Drawing Sheet

BACKGROUND OF THE NEW PLANT

This new poinsettia cultivar originated as a sport of 'Angelika' (U.S. Plant. Pat. No. 5,492) in my greenhouse in Blanzac, France in 1993. It was selected, because of its even growth, uniform branching and more rounded leaves and bracts than 'Angelika'. These are traits that make 'Sophie' more desirable for commercial greenhouse production than 'Angelika'. After selection, 'Sophie' was vegetatively reproduced from stem cuttings for test purposes in Encinitas, Calif. By subjecting clones of this plant to successive generations of vegetative propagation, it was demonstrated that the distinctive characteristics of 'Sophie' held true from generation to generation. Grown under the same greenhouse environment, 'Sophie' had the same flowering response time as the parent plant 'Angelika'.

DESCRIPTION OF THE PHOTOGRAPHS

Poinsettia 'Sophie' is illustrated in the accompanying color photographs.

The upper photo is a side view of one branched plant per pot in full flower.

The lower photo is a top view of the same plant showing flower and bract formation.

DESCRIPTION OF THE PLANT

The following is a detailed description of this new poinsettia as observed in Encinias, Calif., USA during December 1994. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Sophie' and its parent poinsettia 'Angelika' (U.S. Plant Pat. No. 5,492).

| Plant | 'Sophie' | 'Angelika' |
|---|---|---|
| Branching | Uniform length | Uneven length |
| Leaf dimensions | 12 × 8 cm | 14 × 8 cm |
| Bract dimensions | 13 × 9 cm | 15 × 9 cm |
| Bract color | RHS 45B-C | RHS 45A-46B |

Origin: Sport of 'Angelika' (U.S. Plant Pat. No. 5,492).

Classification:

*Botanical.*—*Euphorbia pulcherrima* Willd.

Form: Shrub.

Height: Medium.

Growth habit: As a single stemmed plant, upright and vigorous with self-branching side shoots. The application of a chemical growth retardant may be needed to restrict height for commercial pot plant production. I observed one branched plant in a pot with an overall height of 43 cm and an overall width of 55 cm. The bract diameter of individual flowers was 25 cm.

Branching: Axillary branches will develop and terminate in a flower without pinching. However, it is usually desirable to pinch 'Sophie' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of 16°–18° C. Like its parent, ('Angelika'), 'Sophie' will be in full bloom in late November in the northern hemisphere under natural daylength conditions.

Foliage: The foliage was clean and uniformly dark green from bottom to top of the plant. The leaves were of medium size, leaf blades typically being 12 cm long and 8 cm wide with leaf petioles 5 cm long. The upper and under surfaces of the leaf petiole are red.

*Leaf shape.*—Typical leaves are ovate with obtuse to acute bases and acuminate tips. Leaf margins are mostly entire. An occasional lower leaf is modestly lobed on either side of the leaf blade.

*Leaf surface.*—The upper surface is glabrous and the under surface is finely pubescent.

*Color.*—Upper side — Green, near R.H.S. 147A. Under side — Green, near R.H.S. 147B.

*Retention.*—The foliage retention is good even under low light intensities in the consumer's home.

Bracts: Generally there were 15–17 bright red bracts of various sizes subtending the cyathia. The primary bracts had blades typically 13 cm long and 8–9 cm wide with petioles 2–3 cm long.

*Shape.*—Primary bracts are ovate with acute bases and acuminate tips. Leaf margins are entire or weakly lobed with 1 small indentation on either side of the bract. Secondary bracts are ovate to elliptic and have entire margins.

*Surface.*—The bract surface is slightly rugose.

*Color.*—Upper side — Bright, light red, R.H.S. 45B-C. Under side — Light red, near R.H.S. 45C.

Flowers: Generally, 15–16 cyathia (flowers) were present when the plant was in full bloom. Each cyathium is about 6 mm long and 5 mm wide, green in color, and fringed red at the distal end. Sometimes one but mostly two yellow nectar cups protrude from the side of each cyanthium. The flower pedicel is also green and about 5 mm in length. The stamens protruding from the cyathia are red. The stigmas are red and trifurcate. The pollen is yellow and copious. Cyathia retention was bout three weeks beyond the time the flower was fully mature.

*Nectar exudate.*—Present, abundant.

*Seed formation.*—Self-incompatible.

*Fertility.*—Not observed.

Post production: 'Sophie' was resistant to epinasty after being confined to shipping containers. The foliage and bract retention were good.

What is claimed is:

1. A new and distinct variety of Poinsettia plant, substantially as herein shown and described, distinguished by its strong even growth habit, rounded red flower bracts, self branching and good leaf and bract retention in the consumer environment.

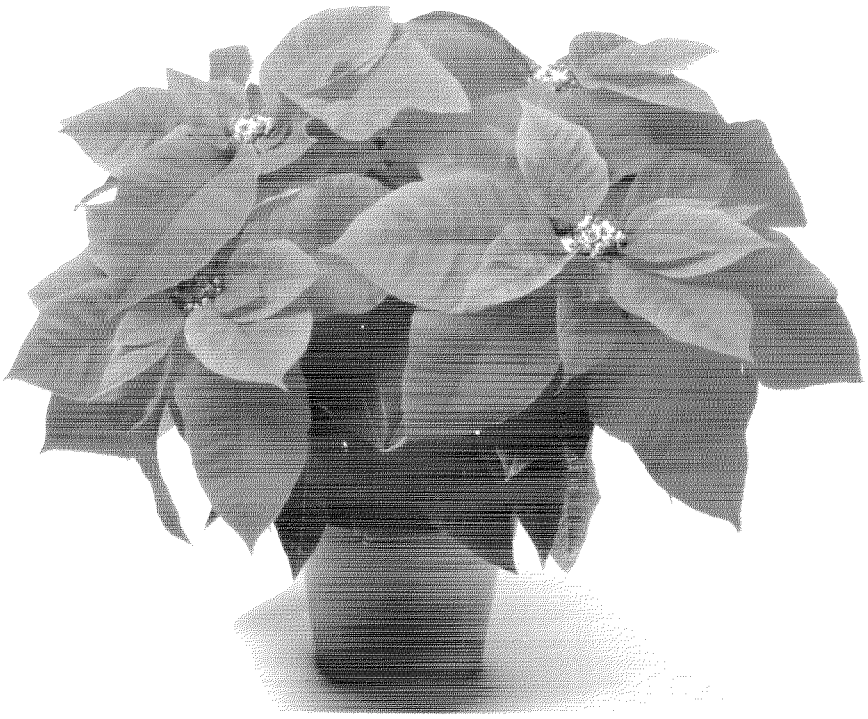
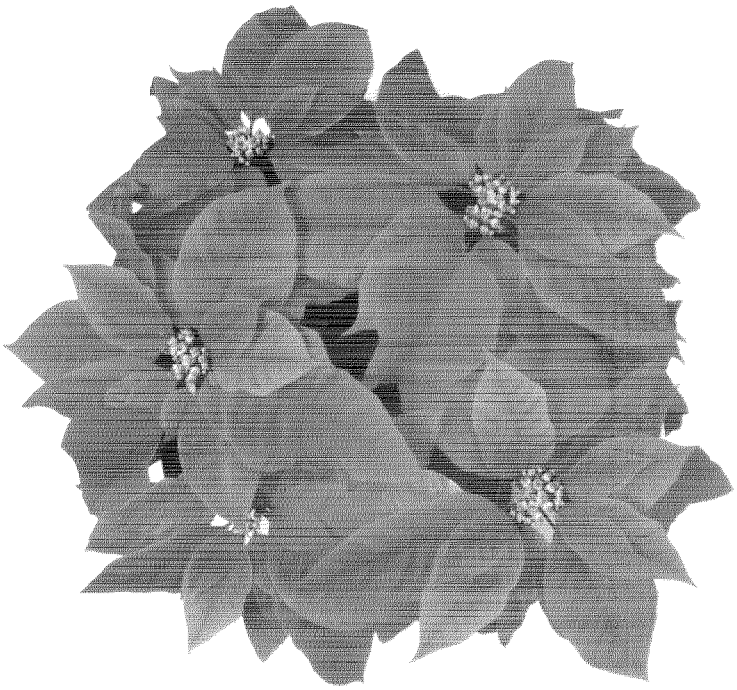

* * * * *